(12) United States Patent
Fladoos

(10) Patent No.: US 11,723,810 B2
(45) Date of Patent: Aug. 15, 2023

(54) MODULAR PHYSIO TAPE WITH THERMAL PROPERTIES

(71) Applicant: Jason Fladoos, Santa Monica, CA (US)

(72) Inventor: Jason Fladoos, Santa Monica, CA (US)

( * ) Notice: Subject to any disclaimer, the term of this patent is extended or adjusted under 35 U.S.C. 154(b) by 240 days.

(21) Appl. No.: 15/931,753

(22) Filed: May 14, 2020

(65) Prior Publication Data
US 2021/0353471 A1    Nov. 18, 2021

(51) Int. Cl.
*A61F 13/04* (2006.01)
*A61F 7/00* (2006.01)
*A61F 13/02* (2006.01)
*A61F 13/00* (2006.01)

(52) U.S. Cl.
CPC ............ *A61F 13/046* (2013.01); *A61F 7/007* (2013.01); *A61F 13/023* (2013.01); *A61F 2007/0071* (2013.01); *A61F 2007/0078* (2013.01); *A61F 2013/00489* (2013.01); *A61F 2013/00655* (2013.01)

(58) Field of Classification Search
CPC .......... A61F 13/0273; A61F 7/03; A61F 7/10; A61F 7/0241; A61F 7/007; A61F 2007/0225; A61F 2007/0226; A61F 2007/0078; A61F 2007/0071; A61F 13/0283; A61F 13/046; A61F 5/0104; A61F 2013/00655; A61F 2013/00489; A61F 13/023; A61F 7/106; A61F 2007/0219; A61F 2013/00187; A61F 13/00051; H05B 3/0023; H05B 3/06; H05B 3/34; H05B 2203/036; A61L 15/14; A61L 15/12
See application file for complete search history.

(56) References Cited

U.S. PATENT DOCUMENTS

| | | | | |
|---|---|---|---|---|
| 3,574,018 A * | 4/1971 | Fujisawa | ................. | A45C 11/00 156/66 |
| 5,302,806 A * | 4/1994 | Simmons | ........... | A41D 13/0051 219/211 |
| 5,545,190 A * | 8/1996 | Meguro | .................. | A61F 7/007 607/96 |
| 5,928,275 A * | 7/1999 | Yates | ...................... | A61F 7/034 126/204 |

(Continued)

*Primary Examiner* — Tarla R Patel
(74) *Attorney, Agent, or Firm* — Benman, Brown & Williams

(57) ABSTRACT

A modular kinesiology or physio tape adapted to produce heating or cooling. The tape includes a layer of material having a chamber for retention and release of a removable packet of cooling or heating material and a mechanism for securing the layer directly onto skin of a user. The removable packet of cooling or heating material has dimensions optimized for manual insertion into and removal from the chamber. Preferably, the material is flexible and includes an adhesive for securing the layer to the skin. The material has a first surface for contacting skin, a second surface parallel to the first surface for receiving and retaining the removable packet and an edge between the first and second surfaces. In one embodiment, multiple slits are provided in the second surface having dimensions adapted to receive and retain said packet. In yet another embodiment, a heating packet is implemented with a button/coin type battery circuit with an optional mechanism for controlling the generation of heat thereby.

13 Claims, 11 Drawing Sheets

(56) References Cited

U.S. PATENT DOCUMENTS

| | | | | |
|---|---|---|---|---|
| 6,713,660 B1* | 3/2004 | Roe | ............... | G01N 33/54366 |
| | | | | 604/361 |
| 9,387,339 B2* | 7/2016 | Sham | ............... | A61N 2/002 |
| 2007/0106354 A1* | 5/2007 | Carstens | ............... | A61F 7/03 |
| | | | | 607/112 |
| 2010/0234785 A1* | 9/2010 | Liebowitz | ............ | A61F 5/0118 |
| | | | | 602/61 |
| 2016/0051393 A1* | 2/2016 | Hahn | ............... | C09J 7/21 |
| | | | | 602/1 |
| 2018/0289530 A1* | 10/2018 | Van Den Dries | ....... | A61F 13/02 |

* cited by examiner

Figure 3e
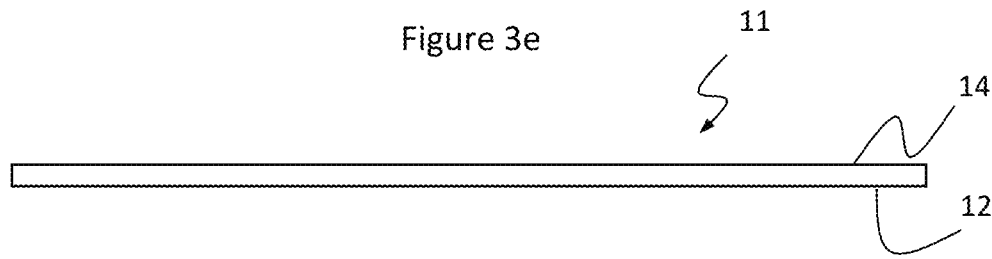
Figure 3f
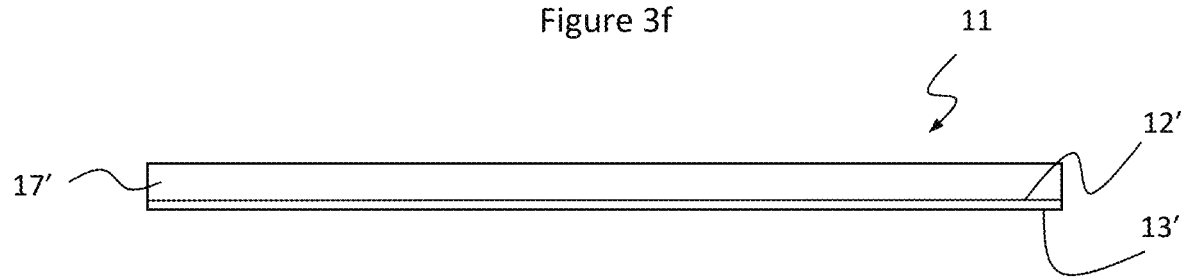
Figure 3g  Figure 3h  Figure 3i
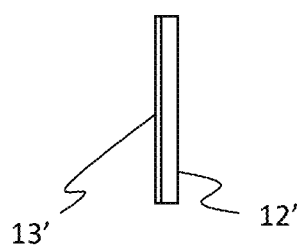 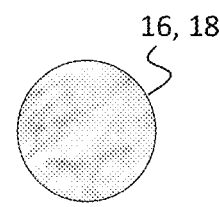 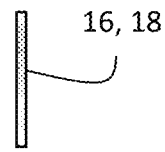
Figure 4a
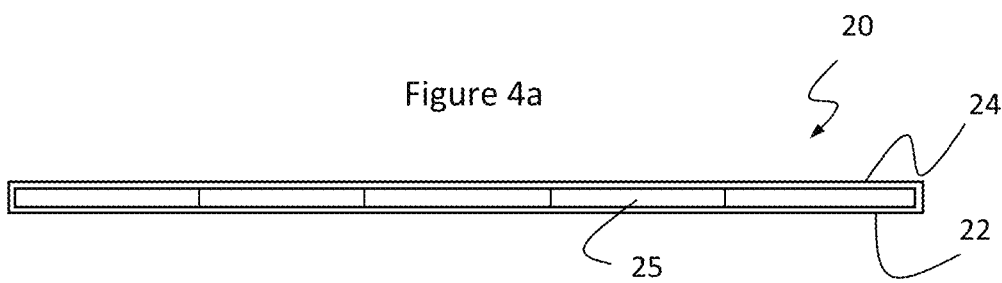
Figure 4b
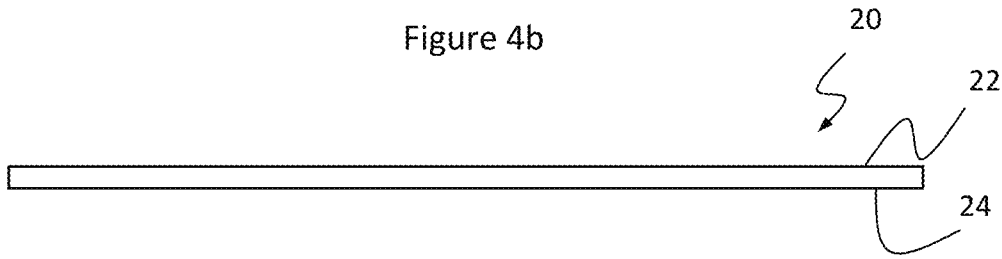

Figure 4g
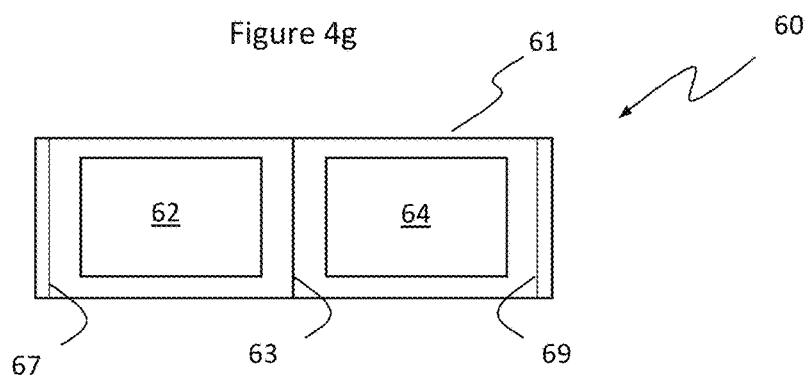
Figure 4h
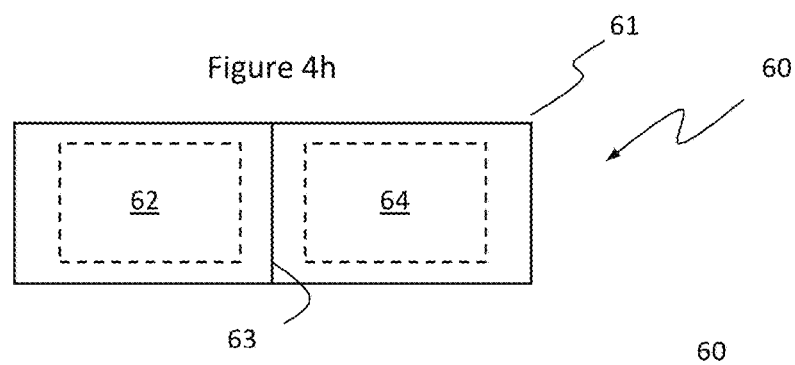
Figure 4i
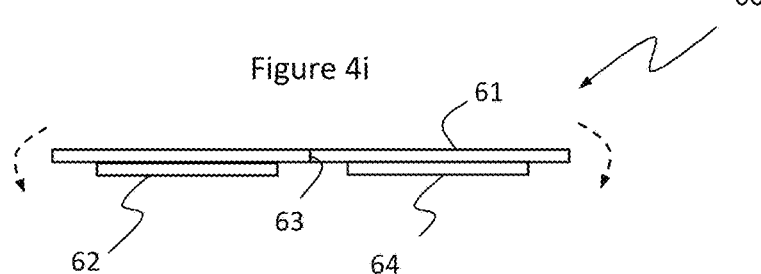
Figure 4j    Figure 4k    Figure 4l    Figure 4m    Figure 4n
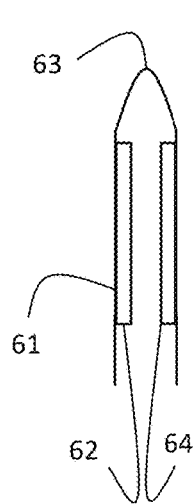 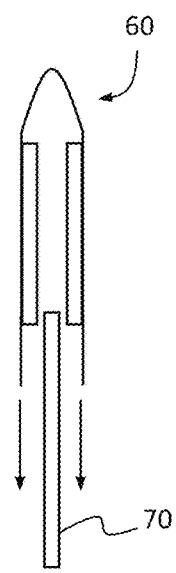 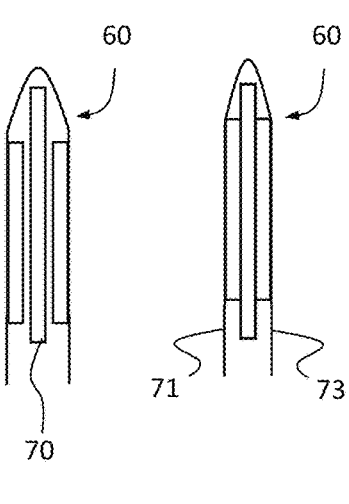

Figure 8
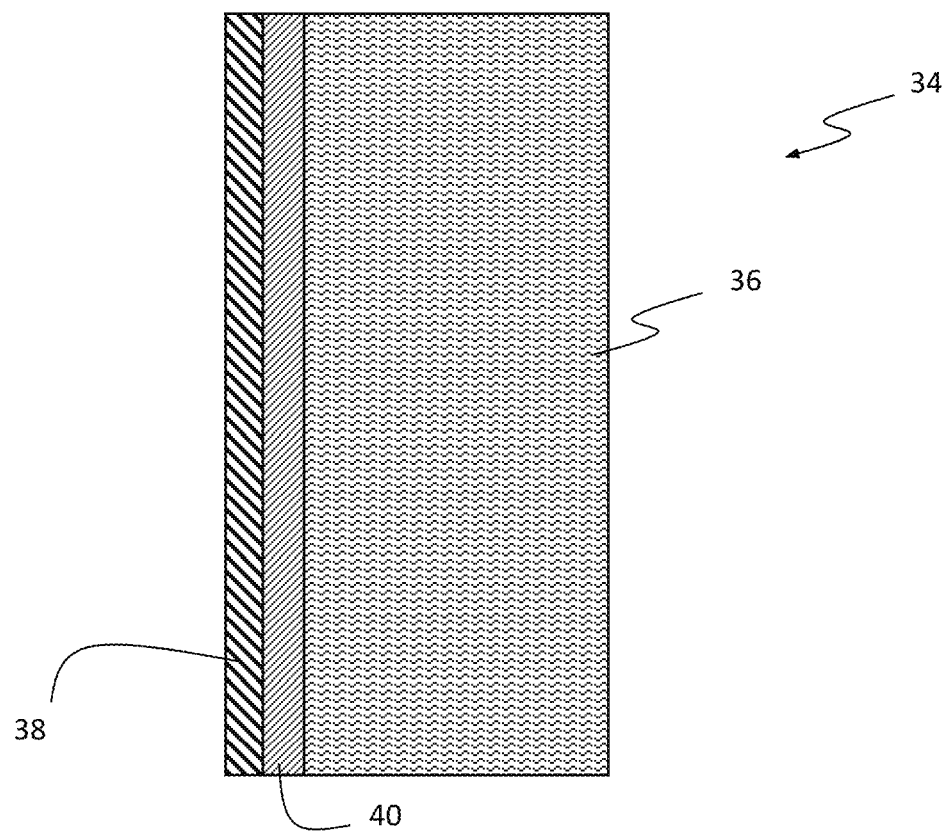
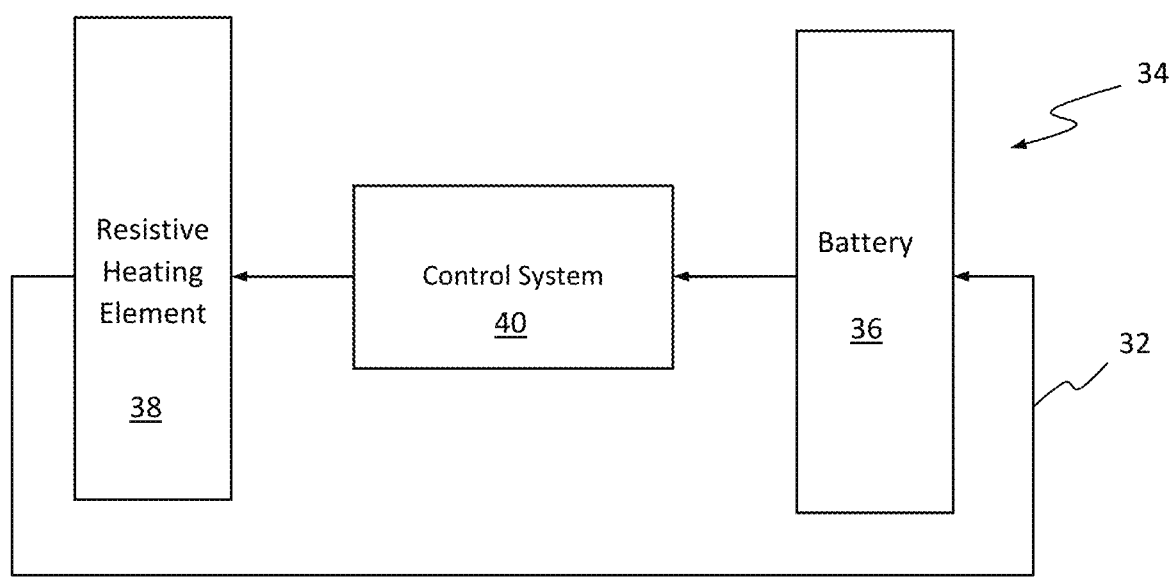
Figure 9

MODULAR PHYSIO TAPE WITH THERMAL PROPERTIES

BACKGROUND OF THE INVENTION

Field of the Invention

The present invention relates to tapes and bindings. More specifically, the present invention relates to therapeutic physio and kinesiology tapes and bindings.

Description of the Related Art

Physio tape (aka kinesiology tape) is a tape that is used for treating athletic injuries and a variety of physical disorders. Physio tape is conventionally a thin, stretchy, elastic cotton strip with an acrylic adhesive. Therapeutic physio tape can be used to treat inflammation as well as a wide variety of musculoskeletal and sports injuries. Physio tape may be manufactured to emulate human skin in both thickness and elasticity to allow the tape to be worn without binding, constriction or restriction of movement.

Physio tapes generally provide support. However, therapists are likely to appreciate that there is a need in the art for a tape that provides support as well as thermal properties such as heat or cold.

The need in the art was addressed by U.S. Pat. No. 10,492,957 entitled Flexible Adhesive Physio Tape with Thermal Properties, issued Dec. 3, 2019 to J. Fladoos (hereinafter 'Fladoos-1'); U.S. Pat. No. 10,350,109 entitled Flexible Adhesive Physio Tape with Cooling Properties, issued Jul. 16, 2019 to J. Fladoos (hereinafter 'Fladoos-2'); and U.S. Pat. No. 10,342,889 entitled Electrically Actuated Adhesive Physio Tape with Thermal Properties, issued Jul. 9, 2019 to J. Fladoos (hereinafter 'Fladoos-3') the teachings of all of which are hereby incorporated by reference herein.

These applications disclose and claim various physio tape designs with thermal heating and cooling properties. While these designs substantially addressed the need in the art, a further need remains for a more cost effective modular physio tape design and construction with removable, replaceable, and interchangeable thermal heating and/or cooling elements.

SUMMARY OF THE INVENTION

The need in the art is addressed by the modular kinesiology or physio tape adapted to produce heating or cooling of the present invention. The inventive tape includes a layer of material having a chamber for retention and release of a removable packet of cooling or heating material and a mechanism for securing the layer directly onto skin of a user. The removable packet of cooling or heating material has dimensions optimized for manual insertion into and removal from the chamber.

Preferably, the material is flexible and includes an adhesive for securing the layer to the skin. The material has a first surface for contacting skin, a second surface parallel to the first surface for receiving and retaining the removable packet and an edge between the first and second surfaces.

In one embodiment, multiple slits are provided in the second surface having dimensions adapted to receive and retain said packet. Each of the slits may be parallel or orthogonal to the edge. In a more specific embodiment, slits are provided in the second surface that intersect in a criss-cross manner to receive and retain the packet horizontally or vertically.

A plurality of slits may be provided in the second surface parallel to the edge surface having dimensions adapted to receive and retain the packet along with a plurality of slits orthogonal relative to the edge having dimensions adapted to receive and retain the packet.

In the best mode, the layer has a first surface for contacting skin, a second surface parallel to the first surface providing a chamber between the first and second surfaces for retaining and releasing the removable packet and an edge between the first and second surfaces. The edge has an aperture therein operationally coupled to the chamber whereby the packet may be deposited into a pocket in the chamber.

In yet another embodiment, a heating packet is implemented with a button/coin type battery circuit with an optional mechanism for controlling the generation of heat thereby.

BRIEF DESCRIPTION OF THE DRAWINGS

FIG. 3d is a top view of the modular kinesiology tape of FIG. 3a.

FIG. 3e is a bottom view of the modular kinesiology tape of FIG. 3a.

FIG. 3f is a magnified sectional top view of an alternative embodiment of the modular kinesiology tape of the present invention with a single adhesive layer and a packet retention layer.

FIG. 3g is a side view of the embodiment of FIG. 3f.

FIG. 3h is a front elevational view of an illustrative embodiment of a packet retained by the modular kinesiology tape of FIG. 3b.

FIG. 3i is a side view of the packet depicted in FIG. 3h.

FIG. 4a is a top view of an alternative embodiment of the kinesiology tape of the present teachings in which insertion of packets from top edges is enabled.

FIG. 4b is a bottom view the alternative embodiment of the kinesiology tape of FIG. 4a.

FIG. 4c is a front view the alternative embodiment of the kinesiology tape of FIG. 4a.

FIG. 4d is a back view the alternative embodiment of the kinesiology tape of FIG. 4a.

FIG. 4e is a side view the alternative embodiment of the kinesiology tape of FIG. 4a.

FIG. 4g is a front elevational view of an illustrative embodiment of a packet hanging arrangement in accordance with the present teachings.

FIG. 4h is a rear elevational view of the illustrative embodiment of a packet hanging arrangement depicted in FIG. 4g.

FIG. 4i is a side elevational view of the illustrative embodiment of a packet hanging arrangement depicted in FIG. 4g in a fully open position.

FIG. 4j is a side elevational view of the illustrative embodiment of a packet hanging arrangement depicted in FIG. 4i in a partially closed position.

FIG. 4k is a side elevational view of the illustrative embodiment of a packet hanging arrangement depicted in FIG. 4j in the partially closed position partially positioned on a section of tape in accordance with the present teachings.

FIG. 4l is a side elevational view of the illustrative embodiment of a packet hanging arrangement depicted in FIG. 4j in the partially closed position fully positioned on a section of tape in accordance with the present teachings.

FIG. 4m is a side elevational view of the illustrative embodiment of a packet hanging arrangement depicted in FIG. 4l in the fully closed and installed position.

FIG. 4n is a side elevational view of the illustrative embodiment of a packet hanging arrangement depicted in FIG. 4m in the fully closed, installed and activated position.

FIG. 8 is a sectional side view of the button/coin battery circuit depicted in FIG. 7 out of the tape pocket.

FIG. 9 is a circuit diagram of the button/coin battery circuit depicted in FIG. 8.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1A:
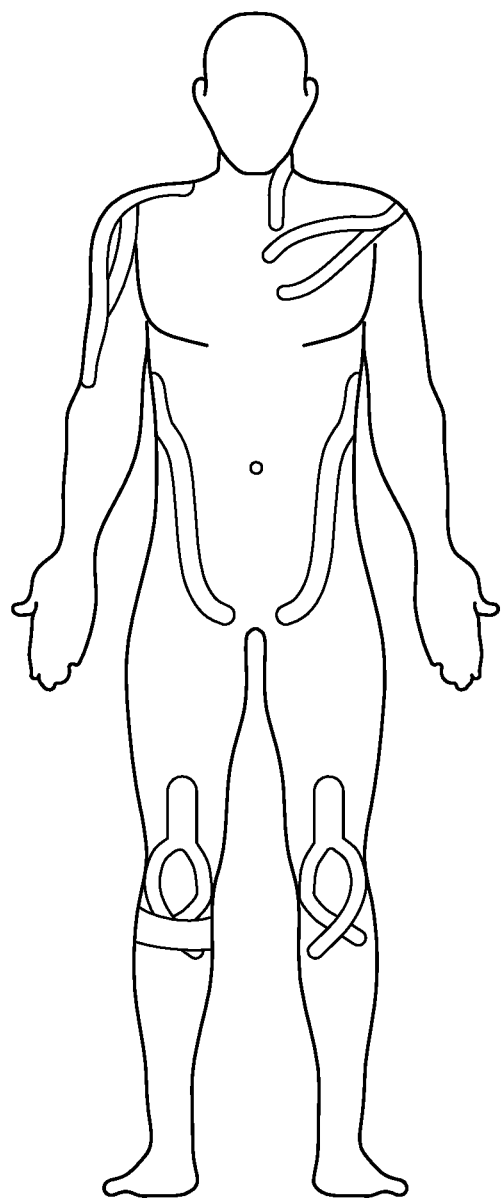
FIG. 1a is a frontal view showing kinesiology tape of conventional design and construction in place on a human body.
Figure 1B:
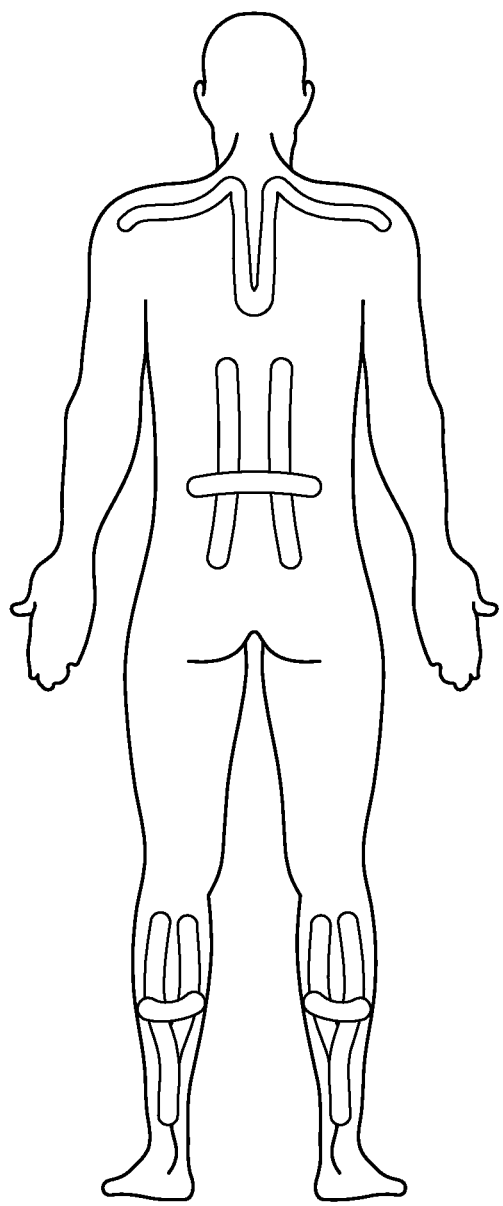
FIG. 1b is a rear view showing kinesiology tape of conventional design and construction in place on a human body.

FIG. 1a is a frontal view showing kinesiology tape of conventional design and construction in place on a human body. FIG. 1b is a rear view showing kinesiology tape of conventional design and construction in place on a human body. As noted above, kinesiology tape of conventional design and construction is not adapted to provide heating or cooling features. The patents incorporated by reference herein address this need. Nonetheless, a need remains for a more cost effective modular physio tape design and construction. This remaining need is addressed by the removable, replaceable, and interchangeable thermal heating and/or cooling elements provided by the modular kinesiology or physio tape of the present invention.

Figure 2A:
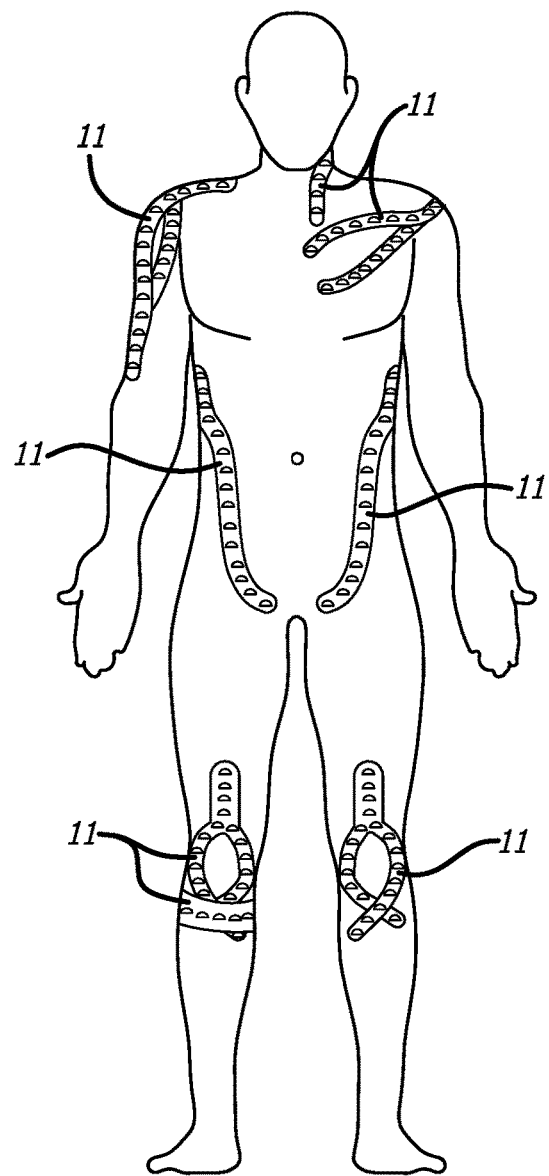
FIG. 2a is a frontal view showing modular kinesiology or physio tape adapted to produce heating or cooling in accordance with the present teachings in place on a human body.
Figure 2B:
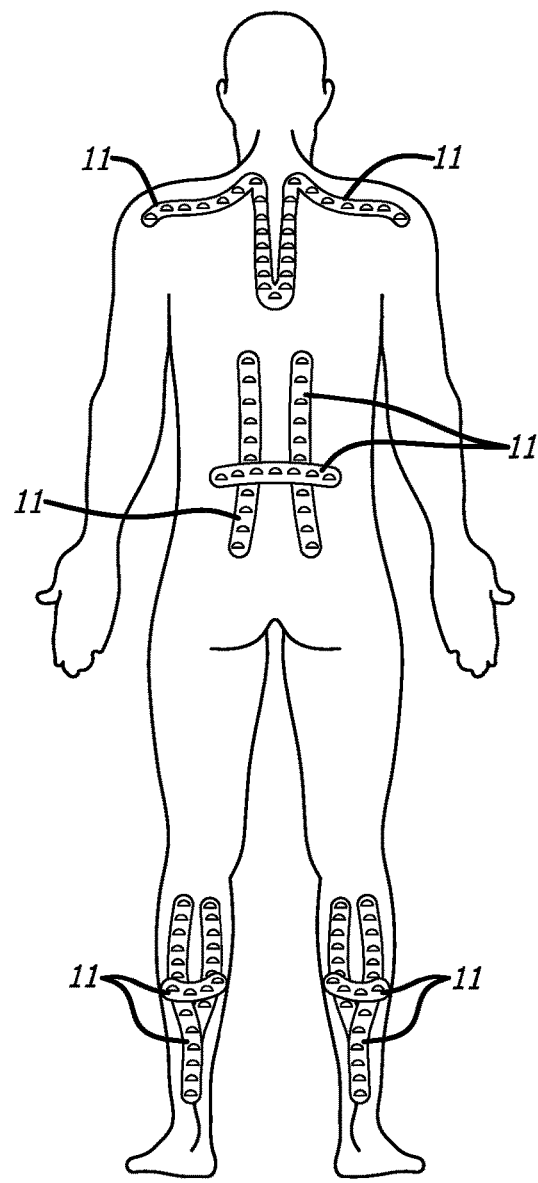
FIG. 2b is a rear view showing modular kinesiology tape adapted to produce heating or cooling in accordance with the present teachings in place on a human body.

FIGS. 2a and 2b are front and rear views showing an illustrative embodiment of the modular kinesiology or physio tape 11 adapted to produce heating or cooling in place on a human body in accordance with the present teachings. These figures illustrate that the tape 11 of the present invention may be used for heating or cooling on the body consistent with the application of conventional kinesiology tape depicted in FIGS. 1a and 1b.

Figure 3A:
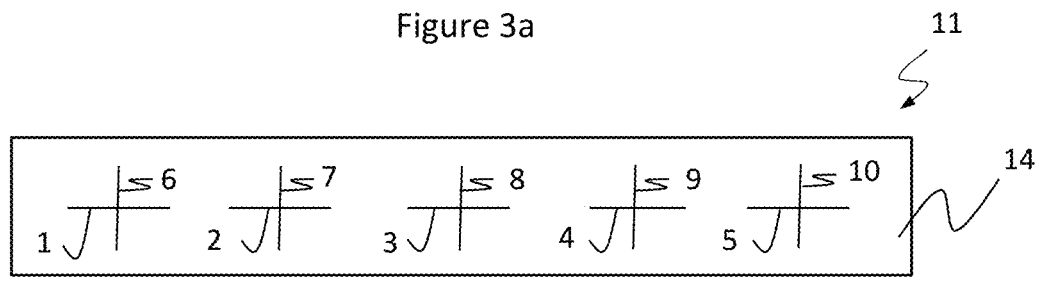
FIG. 3a is a front elevational view of modular kinesiology or physio tape adapted to produce heating or cooling in accordance with the present teachings.

FIG. 3a is a front elevational view of modular kinesiology or physio tape 11 shown in FIGS. 2a and 2b. As disclosed more fully below, in the best mode, if implemented with a single layer, the tape 11 has a first surface 12 for contacting skin, a second surface 14 parallel to the first surface providing a chamber 15 (not shown) therebetween for retaining and releasing a removable heating and/or cooling packet 16, 18 and an upper edge 17 between the first and second surfaces 12 and 14 respectively. As discussed more fully below, in an alternative embodiment, the upper edge 17 has an aperture therein operationally coupled to the chamber whereby the packet may be deposited into the chamber therethrough.

Those of ordinary skill in the art will appreciate that the invention may be implemented with multiple layers in which case, references to 'surfaces' above should be understood to refer to 'layers'.

As disclosed more fully below, a key feature of the present invention is the provision of plural horizontal slits 1-5 and/or vertical slits 6-10 adapted to retain removable, replaceable packets of, active or passive, heating or cooling medium. One of ordinary skill in the art will appreciate that the present invention is not limited to the orientation of the packet retaining slits or the number thereof. The slits may be horizontal, vertical, or intersecting in a crisscross manner without departing from the scope of the present teachings.

Figure 3B:
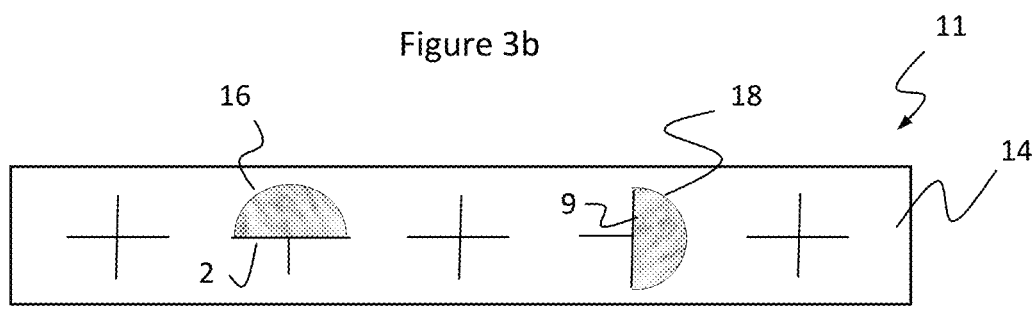
FIG. 3b shows a front view of the modular kinesiology tape of FIG. 3a retaining two packets for heating or cooling in accordance with the present teachings.

FIG. 3b is a front view of the inventive modular kinesiology tape showing a first heating or cooling packet 16 inserted into and retained by the second horizontal slit 2 and a second heating or cooling packet 18 inserted into and retained by the fourth vertical slit 9 in accordance with the present teachings. The remaining slits 1, 3-8 and 10 are unused in FIG. 3b.

Figure 3C:
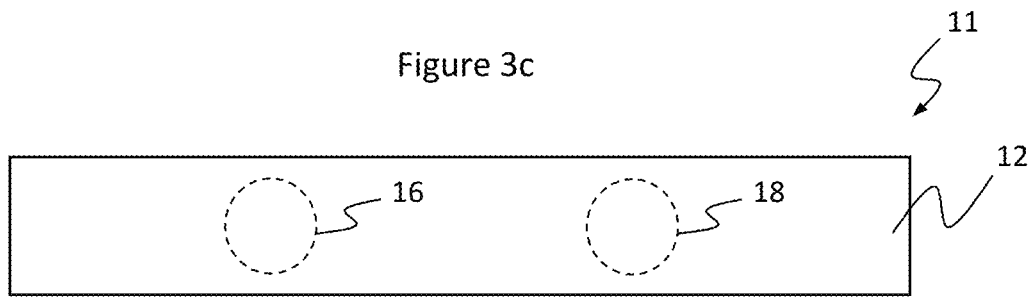
FIG. 3c is a rear view of the modular kinesiology tape of FIG. 3a with two packets shown in phantom.

FIG. 3c is a rear view of the modular kinesiology tape of FIG. 3a with two packets 16, 18 shown in phantom.

Figure 3D:
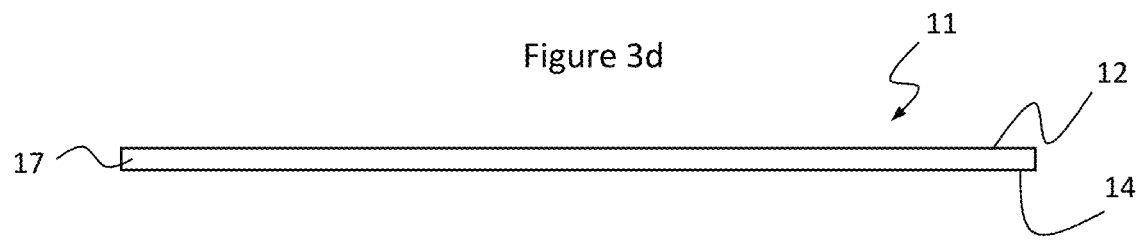

FIG. 3d is a top view of the modular kinesiology tape of FIG. 3a.

FIG. 3e is a bottom view of the modular kinesiology tape of FIG. 3a.

In the best mode, the layer 12 is constructed in accordance with the design and construction disclosed and claimed in Fladoos-1 or Fladoos-2 the teachings of which have been incorporated herein by reference. As an alternative, the layer 12 is constructed of any suitable material such as the flexible adhesive high quality porous fabric typically used in conventional kinesiology tapes.

The material 11 may be implemented as a pad without departing from the scope of the present teachings. In the best mode, when implemented in a tape configuration, the dimensions of the material 11 should be 5-100 cm, 1-10 cm and 3-40 mm in length, width and depth, respectively. On the other hand, in a pad configuration, the material 11 should be 25 cm, 25 cm and 3-40 mm in length, width and depth, respectively.

In any case, those of ordinary skill in the art will appreciate that the present teachings are not limited to the size or shape of the material 11 or the layer 12 nor the number thereof employed.

Preferably, the material 11 is flexible and elastic and includes an adhesive for securing the layer to the skin. The material 11 has a first surface 12 for contacting skin, a second surface 14 parallel to the first surface 12 for receiving and retaining the removable packet 16, 18 and an edge 17 between the first and second surfaces 12 and 14 respectively.

As noted above, in one embodiment, plural horizontal slits 1-5 and/or vertical slits 6-10 adapted to retain removable, replaceable packets of, active or passive, heating or cooling medium. Each of the slits may be parallel or orthogonal to the edge 17. In the best mode, the slits are provided in the second surface intersect in a crisscross manner to receive and retain a packet horizontally or vertically. This provides the user with optimum flexibility in the application of the tape 11.

In another alternative embodiment, the slits on a strip of tape or pad 11 may be of various lengths and depths to accommodate packets of various sizes. And each slit may have an adhesive on an interior surface thereof to assist in packet retention. The second layer may be designed so as to have overlapping open layers to allow for packet insertion.

FIG. 3f is a magnified sectional top view of an alternative embodiment of the modular kinesiology tape 11' of the present invention with a packet retention layer 12' and a single adhesive layer 13'.

FIG. 3g is a side view of the embodiment depicted in FIG. 3f. In the best mode, an acrylic based medical grade adhesive that is gentle on skin is used as the skin adhesive as is common in the industry. However, other adhesives may be used and other arrangements may be used to secure the material 11 or 11' to the skin. For example, adhesive material or as another alternative Velcro may be provided at the ends of the tape to secure the tape to the skin when the tape is wrapped around a user's arm, leg, torso, etc.

FIG. 3h is a front elevational view of an illustrative embodiment of a packet retained by the modular kinesiology tape or pad of FIG. 3b.

FIG. 3i is a side view of the packet depicted in FIG. 3h. The removable packets 16, 18 of cooling or heating material may be implemented with any suitable material having passive (i.e. preheated or precooled) or active (i.e. able to generate heat or cold upon activation) endothermic or exothermic properties depending on the application. In the best mode, the removable heating and cooling packets 16, 18 are implemented in accordance with the teachings of Fladoos-3 the teachings of which are incorporated herein by reference.

Each packet 16, 18 should be optimized in size for manual insertion into and removal from the chamber 14 (not shown) based on the requirements of the application. That is, the packets should have a radius that is less than the slit lengths. Hence, if the packets have a radius of 2 cm, the slits should have a length of at least 2.1 cm and a depth of at least 3 mm. In the best mode, the packets will range in radius from 1.5 cm to 4 cm and have a depth of 2 mm to 40 mm while the slits will have a radius and depth of at least 1.6 cm and 3 mm. When used with in a physio tape application for example, a packet might have dimensions of 2 cm in radius and 10 mm in depth. When used in a pad embodiment of the present teachings, the packets might be 10 cm in radius and 10 mm in depth. Measurement estimations are provided as radius which implies a circle however the pad can also be designed as a square or rectangle with similar dimensions without departing from the scope of the present teachings.

In the best mode, the medium of which the packets are constructed may include endothermic or exothermic reactants, an externally heated or cooled material such as an ice pack or heated gel, an electrical circuit such as a battery and a resistor or an electrical system such as the electrocaloric stack disclosed and claimed in Fladoos-3.

FIG. 4a is a top view of an alternative embodiment of the kinesiology tape 20 of the present teachings in which insertion of packets from top edges is enabled.

FIG. 4b is a bottom view the alternative embodiment of the kinesiology tape of FIG. 4a.

Figure 4C:
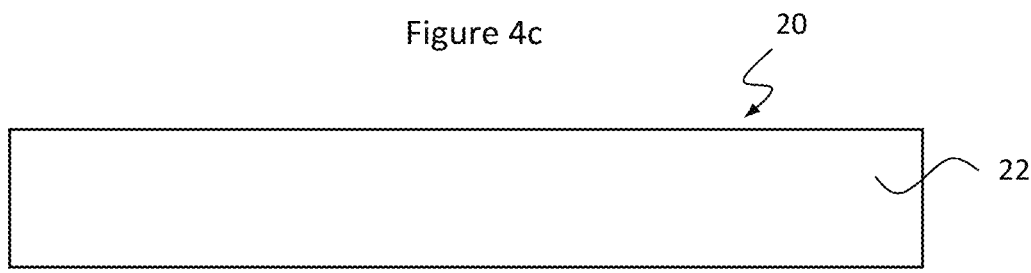

FIG. 4c is a front view the alternative embodiment of the kinesiology tape of FIG. 4a.

Figure 4D:
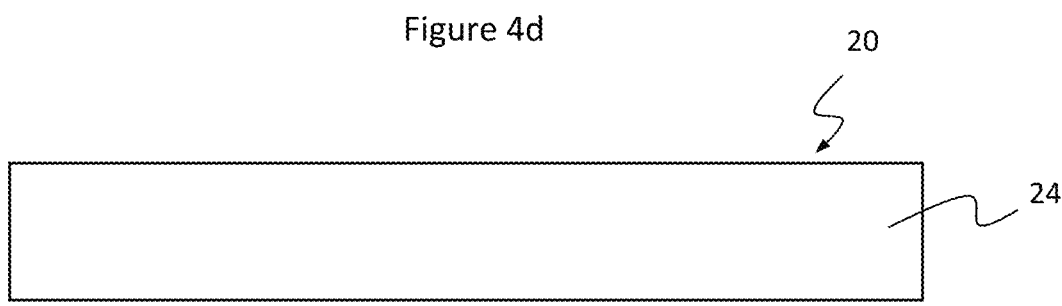

FIG. 4d is a back view the alternative embodiment of the kinesiology tape of FIG. 4a.

Figure 4E:
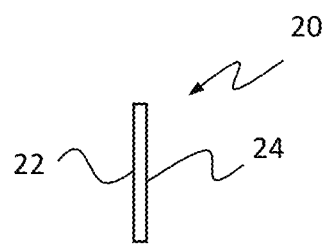

FIG. 4e is a side view the alternative embodiment of the kinesiology tape of FIG. 4a.

In this embodiment, the skin contacting layer 22 and the rear surface 24 are separated to provide plural cavities or chambers 25 therebetween sized to receive and retain packets 26 not shown.

Figure 4F:
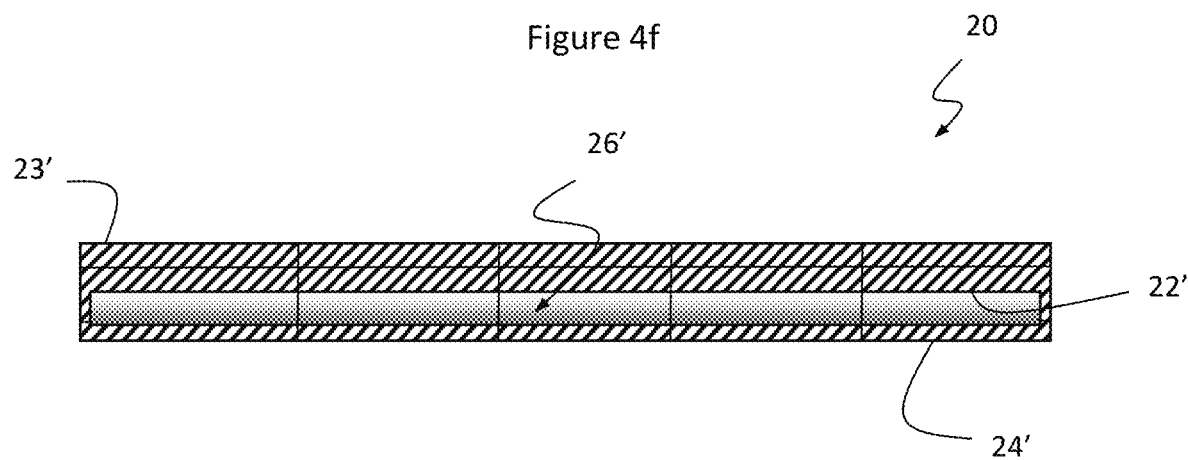
FIG. 4f is a magnified sectional top view of an alternative embodiment of the kinesiology tape of FIG. 4a with at least one saturated heating or cooling layer and a top loading packet retention layer with packets in place in accordance with the present teachings.

FIG. 4f is a magnified sectional top view of an alternative embodiment 20' of the kinesiology tape of FIG. 4a constructed of endothermic or exothermic material implemented in accordance with the teachings of Fladoos-1, Fladoos-2 and Fladoos-3 with an adhesive layer 23' in a top loading packet retention design with packets 26' in place in accordance with the present teachings. With multiple heating or cooling modalities, this embodiment may be expected to provide optimum performance.

It should be noted that the tape may be constructed with a mechanism for retaining the packets that does not require the use of a slit. That is, in accordance with the present teachings, a mechanism may be provided that enables the tape to retain the packets without any attachment at all. The heating or cooling packets can be disposed in a v-shaped receptacle or strap that hangs on the tape and is adapted to snap closed after placement to secure the receptacle with packets on the tape. This is illustrated with respect to FIGS. 4g-4o below.

FIG. 4g is a front elevational view of an illustrative embodiment of a packet hanging arrangement in accordance with the present teachings.

FIG. 4h is a rear elevational view of the illustrative embodiment of a packet hanging arrangement depicted in FIG. 4g.

As shown in FIGS. 4g-h, the packet hanging arrangement 60 consists of a receptacle 61 onto which first and second heating or cooling packets 62 and 64 are mounted. The receptacle 61 may be constructed with plastic, paper or other suitable material. However, for more comfort, in the best mode, the receptacle 61 is kinesiology tape and preferably constructed in accordance with the inventions disclosed and claimed in Fladoos-1 and Fladoos-2, the teachings of which have been incorporated herein by reference. In this case, one or more slits could be employed to hold the packets in the tape, pad or strap 61 in accordance with the present teachings.

The receptacle 61 should be dimensioned based on the application. In the best mode, the receptacle 61 has approximate dimensions of 5 cm in length, 5 cm width and 1 cm in depth. However, the invention is not limited to the size or shape of the packet hanging arrangement. The receptacle 61 has a hinge or seam 63 about which the receptacle can fold as shown in FIGS. 4i-n.

FIG. 4i is a side elevational view of the illustrative embodiment of a packet hanging arrangement depicted in FIG. 4g in a fully open position.

FIG. 4j is a side elevational view of the illustrative embodiment of a packet hanging arrangement depicted in FIG. 4i in a partially closed position.

FIG. 4k is a side elevational view of the illustrative embodiment of a packet hanging arrangement depicted in FIG. 4j in the partially closed position partially positioned on a section of tape in accordance with the present teachings.

FIG. 4l a side elevational view of the illustrative embodiment of a packet hanging arrangement depicted in FIG. 4j in the partially closed position fully positioned on a section of tape in accordance with the present teachings.

FIG. 4m is a side elevational view of the illustrative embodiment of a packet hanging arrangement depicted in FIG. 4l in the fully closed and installed position.

FIG. 4n is a side elevational view of the illustrative embodiment of a packet hanging arrangement depicted in FIG. 4m in the fully closed, installed and activated position.

In use, the packets 62 and 64 are inserted into or affixed to the receptacle 61 using an adhesive such as glue or other suitable adhesive. Paper covers are provided on adhesive on exposed upper surfaces of the packets 62 and 64. The paper covers (not shown) are removed and the receptacle 61 is folded from the position shown in FIG. 4i to the position shown in FIG. 4j. In this position, a small gap is provided between the first and second packets 62 and 64 adapted to allow the arrangement 60 to be positioned on a tape 70 as illustrated in FIG. 4k culminating in the installation on the tape shown in FIG. 4l.

At this point, the user may opt to squeeze both sides of the arrangement 60 causing the cooling or heating elements to be activated if such elements are activated by application of manual pressure. Adhesive may be applied to the exposed surfaces of the packets causing the packets to be secured to the tape 70 when squeezed as shown in FIG. 4m.

In the best mode, the tape 70 is constructed in accordance with the design and construction disclosed and claimed in Fladoos-1 or Fladoos-2 the teachings of which have been incorporated herein by reference. In this case, the cooling or heating efficacy of the packets can be enhanced by the heating or cooling action of the tape 70.

As an alternative, the tape 70 is constructed of any suitable material such as the flexible adhesive high quality porous fabric typically used in conventional kinesiology tapes.

In the best mode, the arrangement 60 is adapted to be sealed after installation on a tape by pinching the distal ends 71 and 73 thereof closed at which time an optional closure mechanism 67 and 69 secures the distal ends in a closed position as shown in FIG. 4n. The closure mechanism may be a simple adhesive, zip lock or other suitable mechanism.

Figure 4O:
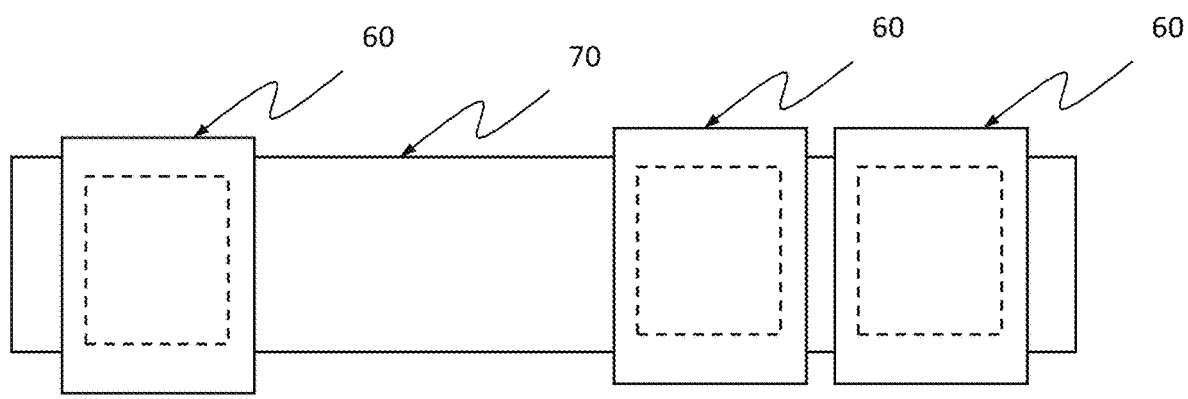
FIG. 4o is a front elevational view showing a plurality of packet hanging arrangements mounted on a tape in various random locations in accordance with the present teachings.

Multiple packet hanging arrangements 60 may be randomly located on the tape 70 per the preferences of the user at the time of application as depicted in front elevational view of FIG. 4o.

While the embodiments disclosed above utilize passive heating or cooling packets, the present invention is not limited thereto. Active heating and cooling elements may be used without departing from the scope of the present teachings.

Figure 5:
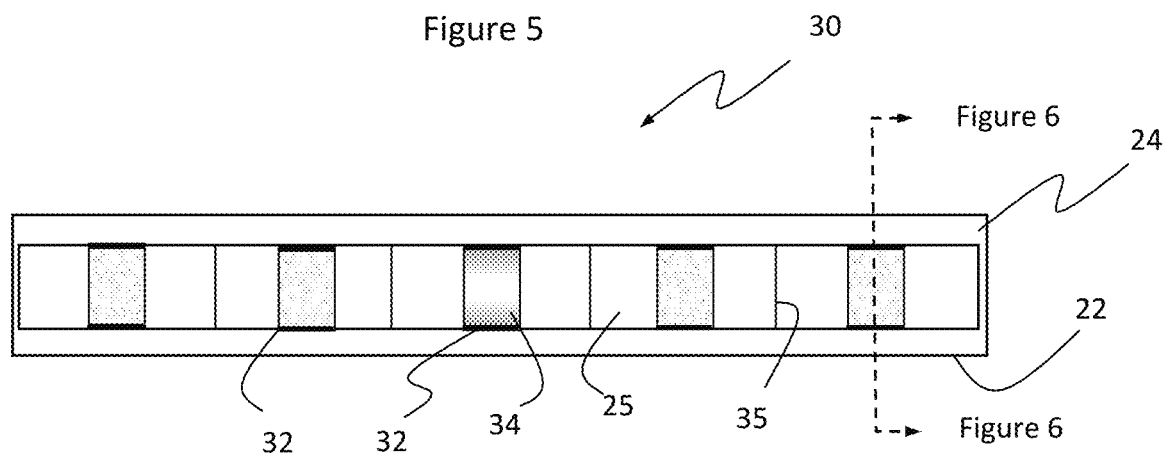
FIG. 5 shows another alternative embodiment in which heating packets are implemented with a lithium button/coin cell battery housed in a resistive holder that makes electrical contact on each side of the battery when the battery is installed therein.

For example, FIG. 5 shows another alternative embodiment 30 in which heating packets are implemented with a lithium button/coin cell battery 34 housed in a resistive holder that makes electrical contact with a connector 32 that contacts each side of the battery 34 when the battery 34 is installed therein.

Figure 6:
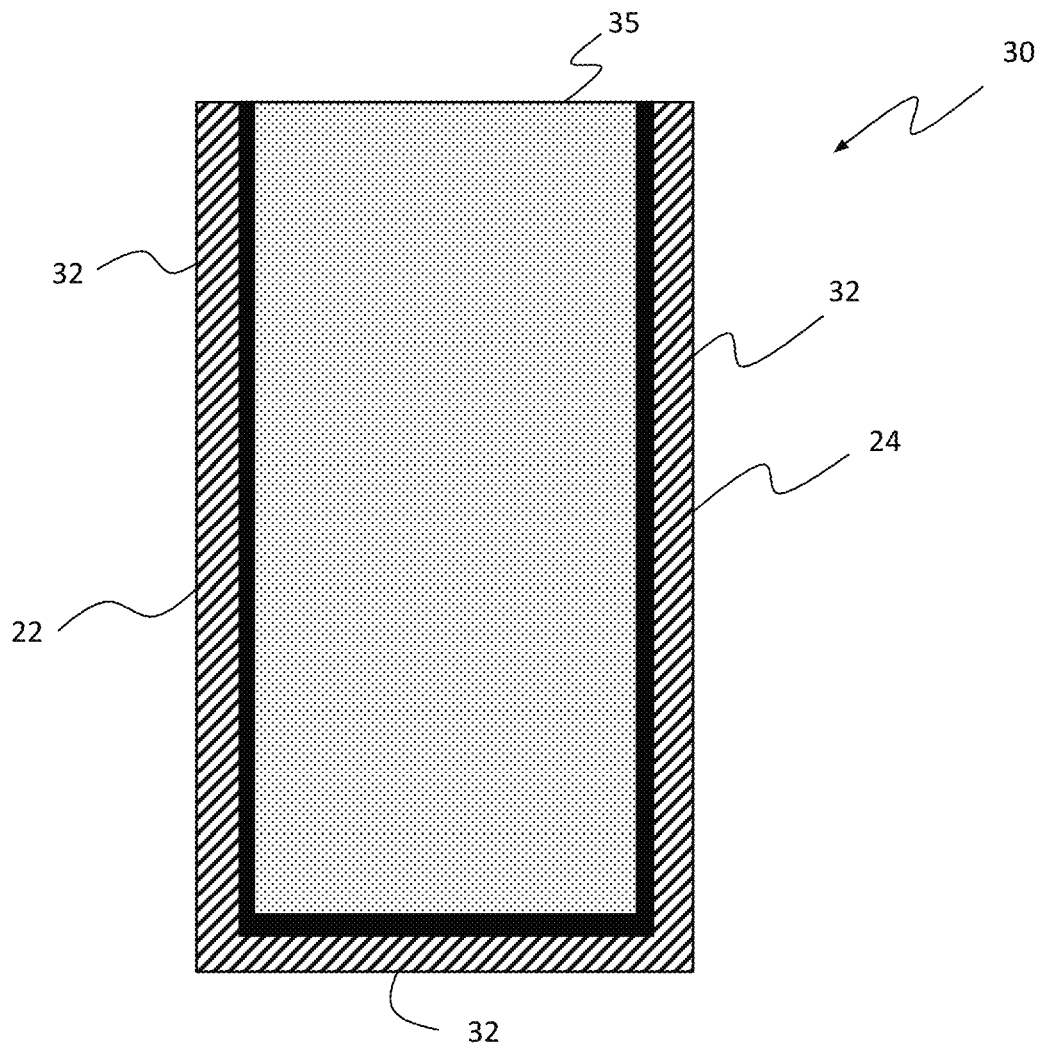
FIG. 6 is an elevated section side view of a pocket of tape shown in FIG. 5 with electrical contacts and without a button/coin cell battery installed therein in accordance with the present teachings.

FIG. 6 is an elevated section side view of a pocket 25 of tape shown in FIG. 5 with electrical contacts 32 and without a button/coin cell battery installed therein in accordance with the present teachings.

Figure 7:
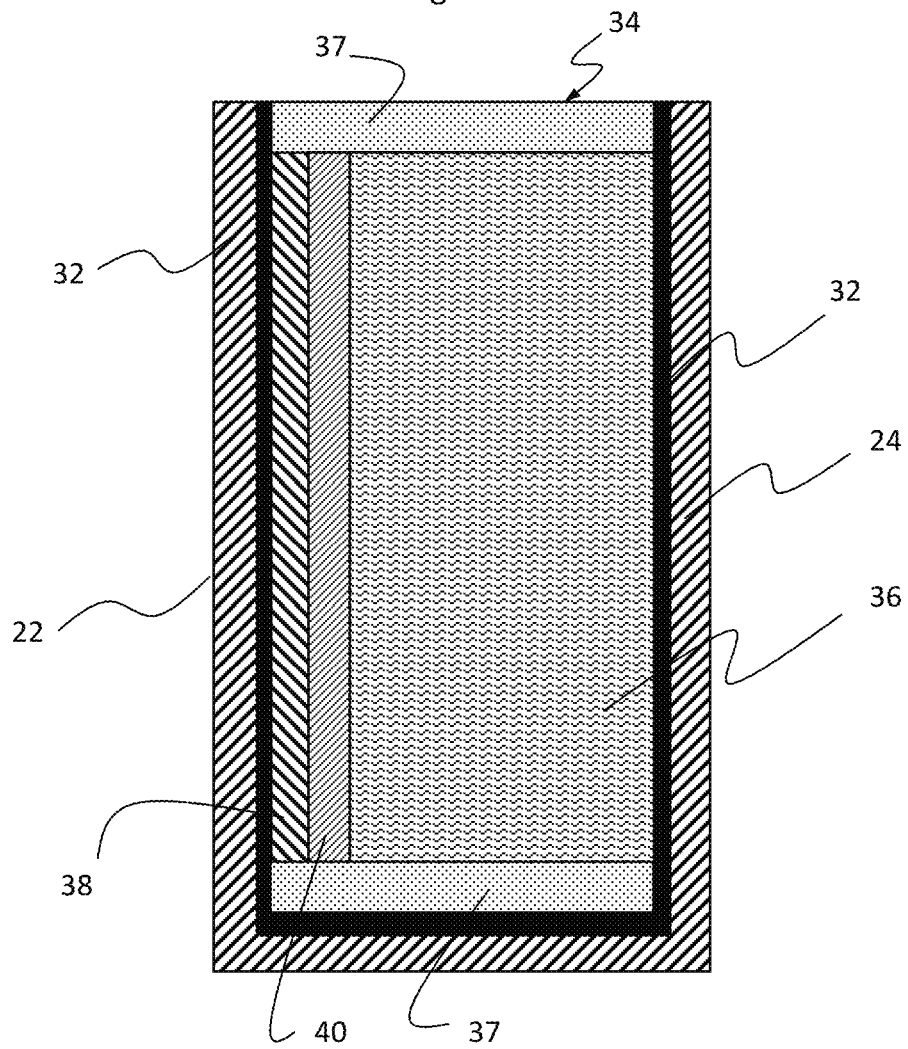
FIG. 7 is an elevated sectional side view of a pocket of the tape shown in FIG. 5 with electrical contacts and a button/coin cell battery installed therein in accordance with the present teachings.

FIG. 7 is an elevated sectional side view of a pocket 25 of the tape 30 shown in FIG. 5 with electrical contacts 32 and a button/coin cell battery 34 installed therein in accordance with the present teachings.

Figure 7A:
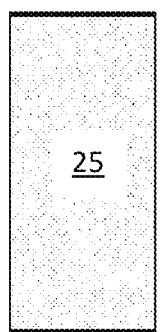
FIG. 7a is a top view of the tape pocket depicted in FIG. 6.

FIG. 7a is a top view of the tape pocket depicted in FIG. 6.

Figure 7B:
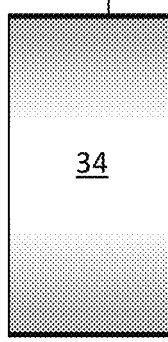
FIG. 7b is a top view of a pocket with a button/coin battery circuit installed therein.

FIG. 7b is a top view of a pocket with a button/coin battery circuit installed therein.

Figure 7C:
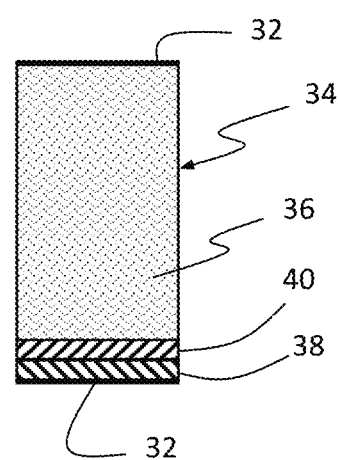
FIG. 7c is a sectional top view of button/coin battery circuit shown in FIG. 7b in accordance with the present teachings.

FIG. 7c is a sectional top view of button/coin battery circuit shown in FIG. 7b in accordance with the present teachings.

FIG. 8 is a sectional side view of the button/coin battery circuit depicted in FIG. 7 out of the tape pocket.

As shown in FIGS. 7-8, the battery circuit can be implemented with a simple battery electrically connected to a resistive element via contact on one terminal or side thereof and to the resistive element via the conductive strip 32 on the other side or terminal thereof. When inserted in the pocket, the electrical strip 32 connects the open terminal of the battery 36 to the open side of the resistive element 38 causing current to flow from the battery 36 through the contact 32 and into the resistive element 38. Current flow through the resistive element then generates heat.

As an alternative, the conductive strip 32 may be integrated into the tape or pad. The resistive element 38 may be implemented with a thin sheet of conductive material such as foil, sized to seat in or be glued into optional grooves within one or more pockets or slits of the tape or pad.

As discussed more fully below, additional circuitry could be included within the packet to provide timing functions, wireless communication to a cell phone for control functions, etc. This is illustrated in FIG. 9.

FIG. 9 is a circuit diagram of an alternative embodiment of the button/coin battery circuit depicted in FIG. 8 with the addition of a control system 40 in accordance with the present teachings.

Figure 10:
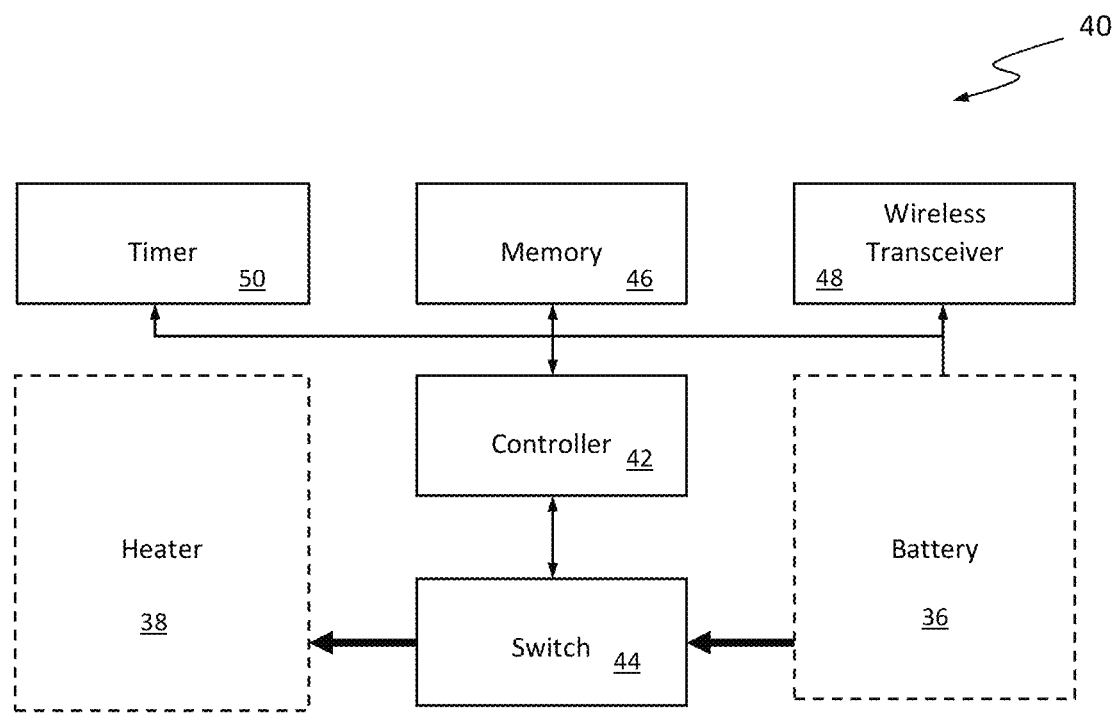
FIG. 10 is a more detailed diagram showing an illustrative embodiment of the control system of the button/coin battery circuit depicted in FIG. 8 in accordance with the present teachings.

FIG. 10 is a more detailed block diagram showing the alternative embodiment of the control system 40 of the button/coin battery circuit depicted in FIG. 9 in accordance with the present teachings. As shown in FIG. 10, the control system 40 includes a controller 42. The controller 42 may be implemented with a simple programmable logic array, analog circuit or processor. The controller 42 is powered by the battery 36 and controls the flow of current from the battery 36 to the resistive element 38 through a relay switch 44. The controller executes code and/or stores data provided by a memory 46. User input and output may be exchanged via a wireless transceiver 48 and used to effectuate control of the system. User inputs are used by the controller to set an optional timer 50 for activation of the switch 44.

The embodiments disclosed above envision heating or cooling packets being held by or in disposed in the tape. However, the invention is not limited thereto. Adhesive areas on the tape may be provided to retain the packets. Adhesive may also be utilized inside the slits to further assist in packet retention. In the alternative, adhesive may be provided on a surface of the packets to provide adhesion to the tape. As yet another alternative, in accordance with the present teachings, a mechanism may be provided to enable the packets to be retained on the tape via a snap or press fit attachment using a zip lock, hook and loop (aka Velcro) or other type of snap fit arrangement on the packet and the tape.

The tape may be implemented with a single layer having with or without a skin adhesive and with an adhesive patch to hold cooling or heating packets in accordance with the present teachings.

The edge accessed pockets could be sealed with adhesive or other means such as zip lock, magnetic, hook and loop or other type fasteners without departing from the scope of the present teachings.

The heating and cooling packets can be mounted directly on the skin using one or more shortened segments of tape 11 in FIG. 3b or the arrangement 60 of FIG. 4g. In this case, in the best mode, the packet is mounted on tape material with a skin adhesive allowing the packet to mounted directly on the skin. If the single, double or multiple packets are mounted in a slit or other arrangement as disclosed herein, replacement of the insert while the tape is being worn is enabled as will be apparent to one of ordinary skill in the art. That is, no removal of the tape from the skin is required to replace the heating or cooling element. Hence, 'on the body' replacement of heating or cooling elements is enabled.

It is therefore intended by the appended claims to cover any and all such applications, modifications and embodiments within the scope of the present invention.

The invention claimed is:

1. An adhesive physio-tape adapted to produce heating or cooling comprising:
    an elongate planar, flexible, elastic strip of material with adhesive along the length of an underside thereof and configured for securing the planar strip to a body of a user while the planar strip is in place on the user's skin in a substantially planar orientation, said planar strip having a longitudinal axis between first and second ends thereof,
    at least one pocket disposed along the longitudinal axis of the tape between said first and second ends;
    a removable heating or cooling elements mounted in the pockets,
    a slit in said pocket substantially aligned with the longitudinal axis of the tape to retain the heating or cooling element horizontally,
    whereby the heating or cooling elements may be inserted into the pocket and retained by the pocket or removed from the pocket horizontally.

2. The tape of claim 1 wherein the removable heating or cooling element is a heating element and includes a resistive heating element.

3. The tape of claim 2 wherein the heating element includes a control system for controlling generation of heat by a battery.

4. The tape of claim 3 wherein the control system includes a controller and a switch.

5. The tape of claim 1 wherein the removable heating or cooling element is planar.

6. The tape of claim 1 wherein the material has a first surface for contacting skin, a second surface parallel to the first surface, whereby the pocket is provided for receiving and retaining the removable heating or cooling element between the first and second surfaces.

7. The tape of claim 6 further including at least two slits in the second surface that intersect in a crisscross manner to receive and retain the heating or cooling element either horizontally or vertically.

8. The tape of claim 1 further including a plurality of slits in the material parallel to the longitudinal axis thereof, each slit having dimensions adapted to receive and retain one of said elements.

9. The tape of claim 1 wherein the material has a first surface for contacting skin, a second surface parallel to the first surface providing a chamber or pocket between the first and second surfaces for retaining and releasing the removable heating or cooling element and an edge between the first and second surfaces, said edge having an aperture therein operationally coupled to the chamber whereby the element may be deposited into the chamber therethrough.

10. The tape of claim 9 wherein an electrical conductor is disposed within said chamber or pocket to provide electrical connectivity between one side of a battery circuit and another side thereof.

11. An adhesive physio-tape adapted to produce heating or cooling comprising:
    an elongate planar, flexible, elastic strip of material with adhesive along the length of an underside thereof and configured for securing the planar strip to a body of a user while the planar strip is in place on the user's skin in a substantially planar orientation, said planar strip having a longitudinal axis and a transverse axis between first and second ends thereof,
    at least one pocket disposed along the longitudinal axis of the tape between said first and second ends;
    a removable heating or cooling elements mounted in the pocket,
    a slit in said pocket substantially aligned with the transverse axis of the tape to retain the heating or cooling element vertically,
    whereby the heating or cooling elements may be inserted into the pocket and retained by the pocket or removed from the pocket vertically.

12. The modular tape of claim 11 further including plural pockets disposed along the longitudinal axis of the tape between said first and second ends.

13. A modular tape or pad adapted to produce heating or cooling comprising:
    a planar, flexible, elastic strip of material with adhesive along the length of the underside thereof and configured for securing the planar strip to a body of a user while the planar strip is in place on the user's skin in a substantially planar orientation;
    a planar removable heating or cooling element, wherein the removable heating element includes a resistive heating element and a control system for controlling generation of heat by a battery; and
    a mechanism for securing the heating or cooling element to and removing the heating or cooling element from the planar strip of material.

* * * * *